United States Patent
Hamou et al.

(10) Patent No.: US 8,894,645 B2
(45) Date of Patent: Nov. 25, 2014

(54) MEDICAL RESECTOR HAVING A ROTATABLE HIGH-FREQUENCY ELECTRODE AND DRIVE UNIT THEREFOR

(75) Inventors: Jacques Hamou, Paris (FR); Markus Simmen, Schwerzenbach (CH); Otmar Stillhard, Steckborn (CH)

(73) Assignee: Karl Storz GmbH & Co. KG (DE)

( * ) Notice: Subject to any disclaimer, the term of this patent is extended or adjusted under 35 U.S.C. 154(b) by 1105 days.

(21) Appl. No.: 12/885,098

(22) Filed: Sep. 17, 2010

(65) Prior Publication Data

US 2011/0066148 A1    Mar. 17, 2011

(30) Foreign Application Priority Data

Sep. 17, 2009 (DE) .................. 10 2009 041 605

(51) Int. Cl.
*A61B 18/14* (2006.01)
*A61B 18/18* (2006.01)

(52) U.S. Cl.
CPC ..... *A61B 18/1485* (2013.01); *A61B 2018/1861* (2013.01); *A61B 2018/1407* (2013.01)
USPC .............................. 606/41; 606/45

(58) Field of Classification Search
CPC ............... A61B 2018/00208; A61B 2018/144; A61B 18/149; A61B 17/32003; A61B 2018/00202; A61B 18/14
USPC ............. 606/34, 41, 45, 46; 600/105
See application file for complete search history.

(56) References Cited

U.S. PATENT DOCUMENTS

| 5,133,713 | A | | 7/1992 | Huang et al. | |
|---|---|---|---|---|---|
| 5,910,150 | A | * | 6/1999 | Saadat | 606/159 |
| 5,980,545 | A | * | 11/1999 | Pacala et al. | 606/170 |
| 6,565,561 | B1 | | 5/2003 | Goble et al. | |
| 2003/0149442 | A1 | * | 8/2003 | Gellman et al. | 606/170 |
| 2006/0178670 | A1 | * | 8/2006 | Woloszko et al. | 606/48 |
| 2008/0009855 | A1 | * | 1/2008 | Hamou | 606/46 |
| 2011/0066149 | A1 | * | 3/2011 | Hamou et al. | 606/45 |
| 2011/0196400 | A1 | * | 8/2011 | Robertson et al. | 606/169 |

FOREIGN PATENT DOCUMENTS

| DE | 1759256 U | 1/1958 |
|---|---|---|
| DE | 3313325 A1 | 10/1984 |
| DE | 69824851 T2 | 7/2005 |
| DE | 102006039696 A1 | 2/2008 |
| EP | 0448857 A1 | 10/1991 |
| FR | 2645008 A1 | 10/1990 |
| WO | 2006048199 A1 | 5/2006 |

OTHER PUBLICATIONS

European Search Report; Application No. EP 10 00 9170; Issued: Jul. 8, 2011; 12 pages.

* cited by examiner

*Primary Examiner* — Linda Dvorak
*Assistant Examiner* — Jocelyn D Ram
(74) *Attorney, Agent, or Firm* — St. Onge Steward Johnston & Reens LLC

(57) ABSTRACT

A drive unit for a rotatable high-frequency electrode of a medical resector for cutting, ablating, or coagulating human or animal tissue includes an engine device for generating a rotation movement and a coupling device for transmitting the rotation movement generated by the engine device to an axis coupled with the rotatable high-frequency electrode when the drive unit is coupled with the medical resector. The drive unit is configured to provide on the coupling device a rotation frequency in a range from 10 rpm to 200 rpm.

10 Claims, 2 Drawing Sheets

MEDICAL RESECTOR HAVING A ROTATABLE HIGH-FREQUENCY ELECTRODE AND DRIVE UNIT THEREFOR

CROSS-REFERENCE TO RELATED APPLICATIONS

The present application claims priority of German patent application No. 10 2009 041 605.6 filed on Sep. 17, 2009, the content of which is incorporated herein by reference.

FIELD OF THE INVENTION

The present invention relates to a medical resector having a rotatable high-frequency electrode and a drive unit for a medical resector with a rotatable high-frequency electrode.

BACKGROUND OF THE INVENTION

In high-frequency surgery (HF surgery) an electrode supplied with high-frequency electric current is used for cutting tissue. A high-frequency electrode made of a wire sling is used, for instance, for ablating tissue. The sling is pushed or pulled through the tissue by the operator in order to cut out tissue snippets or shavings of just about any length.

A medical resector developed by Jacques Hamou comprises a rotating wire sling as high-frequency electrode. The wire sling ablates the tissue in the form of small shavings or snippets, for instance similarly to the functioning of a milling head for machined processing of workpieces. Medical resectors of this type are described for instance in WO 2006/048199 A1 and DE 10 2006 039 696 A1. Resection or ablation or the detaching of tissue in small fragments makes possible an immediate visual control, simplified handling, and clean and precise ablation of tissue. In addition, the small portions of tissue are easily removable, for instance by suction integrated in the medical resector.

The rotatable high-frequency electrodes of conventional medical resectors are powered by standard engines used for a wide range of applications in surgery and other medical fields. These standard engines as a rule are equipped with an INTRA coupling according to ISO 3964 and deliver rotation frequencies of several tens of thousands of revolutions per minute. Therefore, a reduction gear is used between the standard engine and the medical resector.

A medical resector as set forth in the following description can be combined with an endoscope to form a resectoscope, in such a way that a shaft of the endoscope is positioned inside a channel in the shaft of the medical resector.

It is an object of the present invention to provide an improved drive device for a rotatable high-frequency electrode of a medical resector and an improved medical resector.

SUMMARY OF THE INVENTION

This object is achieved, in one respect, through a drive unit for a rotatable high-frequency electrode of a medical resector for cutting, ablating, or coagulating human or animal tissue, having: an engine device for generating a rotation movement; a coupling device for transmitting the rotation movement generated by the engine device to an axle coupled with the rotatable high-frequency electrode when the drive unit is coupled with the medical resector, wherein the drive unit is configured to provide on the coupling device a rotation frequency in a range from 10 revolutions per minute to 200 rpm. In another respect, the above noted objects are achieved through a medical resector for cutting, ablating, or coagulating human or animal tissue, having a rotatable high-frequency electrode on the distal end of the medical resector; a coupling device on the proximal end of the medical resector; an axle which connects the coupling device with the high-frequency electrode, wherein the coupling device is configured for detachable mechanical coupling with a drive unit that provides a rotation frequency in a range from 10 rpm to 200 rpm.

Various embodiments of the present invention are based on the idea of providing a drive unit for a rotatable high-frequency electrode of a medical resector for cutting, ablating, or coagulating human or animal tissue, said unit comprising an engine unit for generating a rotation movement and a coupling device for transmitting the rotation movement generated by the engine unit to an axle coupled with the rotatable high-frequency electrode when the drive unit is coupled with the medical resector, wherein said drive unit is configured to provide the coupling device with a rotation frequency in a range that extends from 10 rpm to 200 rpm.

With this drive unit, in particular, all functionalities are integrated in a single housing in order to provide the rotation frequency at which the rotatable high-frequency electrode of a medical resector is to rotate. No doubt it can seem attractive to use a standard engine that is present in nearly every clinic and almost every relevant physician's practice. In fact, as a result, the investments required for using a medical resector with rotatable high-frequency electrode are reduced and in the event of a failure of the standard engine, a quick, problem-free replacement becomes possible by another standard engine. Initial experience with the present invention indicates, however, that the advantages surprisingly are far outweighed by the substantially simplified operation of a drive unit that, rather than having to be first linked to a separate reduction gear, can be immediately connected with a medical resector and its rotatable high-frequency electrode. This improvement in handling refers not just to operation during its use but above all to the cleaning, maintenance, and disinfection or sterilization between two uses.

In particular, the compact drive unit comprises only one mechanical coupling for immediate coupling with an axle of a rotatable high-frequency electrode, which has to be protected, cleaned, and maintained so as to guard against the penetration of fluids or alien material. Additional couplings, for example those required between a standard engine and a reduction gear, are dispensed with. Also absent is the requirement for releasable but sufficiently robust mechanical connection between a standard engine and a reduction gear. In addition, because of the absence of couplings and other mechanical interfaces, the drive unit depending on the expected application can be much more compact, lighter, and more economically produced than a conventional combination of standard engine and external reduction gear.

To ascertain appropriate rotation frequencies or rotation numbers, at first theoretical considerations and computations were employed that were based on experience values with conventional, not rotating sling-shaped high-frequency electrodes. For this type of conventional high-frequency electrodes, depending on the tissue and other conditions of the individual case, a cutting speed of approximately 10 mm per second can be considered as proven. It is assumed that the cutting speed at any spot on the rotating high-frequency electrode should not lie above the proven cutting speed of 10 mm per second.

The cutting speed is also linearly dependent on the radius as well as on the rotation frequency. At a maximum cutting speed of 10 mm per second and at a diameter of the wire sling or of the high-frequency electrode of 4 mm, computations result in a rotation frequency of 48 revolutions per minute, and at 6 mm a rotation frequency of 32 rpm and at 8 mm a rotation frequency of 24 rpm. Extensive, detailed, and therefore also time-consuming experimental investigations by Jacques Hamou confirm that at the usual diameters of high-frequency electrodes or of wire slings at rotation frequencies between 30 rpm and 60 rpm, major advantages are realized, surprisingly not only with respect to the cutting capacity and the cutting quality. Depending on the size and shape of the high-frequency electrode as well as on the tissues to be cut, lower rotation frequencies from about 10 rpm or 20 rpm and higher rotation frequencies up to about 100 rpm, or in an individual case up to 150 rpm or 200 rpm, are advantageous.

Surprisingly, at the aforementioned rotation frequencies, in particular at rotary frequencies between 30 rpm and 60 rpm, an optimum is achieved with respect to the ablation capacity on the one hand and the observability and controllability of ablation on the other hand. Despite a favorable ablation capacity, the ablated tissue pieces are so small that they interfere only slightly with the view of the work area through an endoscope positioned, for instance, in the resector. The slight negative impact on the view through the endoscope is also based on the fact that the tissue pieces can be suctioned out and thus removed from the field of vision quickly and without the risk of clogging the medical resector.

Surprisingly, the rotation frequency of the rotatable high-frequency electrode also plays an important role in the impact on medical personnel and thus in turn indirectly in the quality of the achieved result. At the aforementioned rotation frequencies, especially at rotation frequencies up to 60 rpm, the movement of the high-frequency electrode can still be perceived by the eye of medical personnel without difficulty and halted. Observation of the high-frequency electrode is therefore not yet perceived as stressful. Every individual ablated tissue piece and the resulting exposed deeper tissue layers and their surfaces can be pursued or observed. At clearly higher rotation frequencies above 100 rpm and higher, at more than 200 rpm, the movement of the high-frequency electrode and of the tissue pieces and their observation prove increasingly tiring. This is hazardous for medical applications not only involving the medical personnel but also, above all, for the patient.

In addition, at the aforementioned rotation frequencies, in particular in the range of 30 rpm to 60 rpm, the ablation can be especially well controlled. The described good observability on the one hand and the sufficiently rapid but not too rapid ablation are apparently especially suited for control and regulation of the ablation by medical personnel.

The aforementioned advantages are achieved thus and, especially also in this combination, at no other rotation frequency. Lower rotation frequencies result in an insufficient ablation capacity. In addition, the individual ablated tissue fragments are too large to be suctioned off perfectly. Moreover, the tissue fragments cover the exposed tissue layers too long before they are completely detached and removed, for instance by suction, from the field of vision.

At higher rotation frequencies above 200 rpm, depending on the tissue, often even at rotation frequencies over 100 rpm or over 60 rpm, the quality of the cuts, in particular the coagulation, is often insufficient. In addition, the observation of the rapid movements is tiring for the eye of medical personnel. Depending on the tissue, in addition, the ablated tissue pieces can be too small so that they cling in particular to surfaces and can be suctioned off only with difficulty.

Corresponding computations were also made for the feed rate. At a rotation frequency of 50 rpm and a feed of 5 mm per second, the result is a cutting depth or shaving thickness of 3 mm. Reflections and investigations into the shape of a sling-shaped high-frequency electrode led to a circular or elliptical or oval shape, where the sling lies in one plane. With an elliptical or oval form, the small main axis is positioned parallel to the rotation axis; in particular, the small main axis coincides with the rotation axis.

In order to achieve on the coupling device a rotation frequency ranging from 10 rpm to 200 rpm, the aforementioned drive unit in particular comprises an integrated reduction gear. The reduction gear and engine are in particular firmly flanged onto one another or have a common housing. The integration of a reduction gear into the drive unit makes possible an optimal adaptation of said unit to the engine. In using an engine that yields the necessary capacity in a rotation frequency of a few thousand revolutions per minute, a decidedly lower reduction is required than with the conventionally used standard engines with approximately tenfold greater rotation frequency.

Alternatively, the drive unit comprises an engine that produces the required capacity with the aforementioned rotation frequencies, so that no reduction gear is required. In addition, along with a slow-running electrical, hydraulic, or pneumatic engine, it is possible to use an ultrasound engine in particular. The entire absence of a reduction gear is optimal with respect to the size and mass of the drive unit as well as the sound produced during operation, and reduces play to a minimum.

The coupling device can include a hollow space with a cylindrical (but not as a rule circular-cylindrical) portion that is not symmetrical to the rotation axis of the coupling device. A cylindrical portion is a portion that is cylindrical or essentially cylindrical. The cylindrical portion thus is not symmetrical to the rotation axis of the coupling device if departures from symmetry are caused not only by cams or the like, as these are sometimes employed with conventional coupling devices as a tappet or for catch locking.

In this cylindrical hollow space a correspondingly configured portion can engage with a corresponding coupling device of the medical resector. The cylindrical hollow space has a cross-section, for example, whose border includes a straight portion.

For example, the border of a semicircular cross-section has a straight portion. A coupling device with a cross-section of this kind consists, for example, of a tube with a lumen with a circular cross-section, so that a semicircular cylindrical body is inserted in the lumen of the tube. The semicircular cylindrical body comprises a semicircular-shaped cross-section with an arc-shaped border portion and a straight border portion. The arc-shaped portion of the border of the cross-section of this body has the same radius as the cross-section of the lumen of the tube and is contiguous with the border of the lumen. Then the cross-section of the hollow space remaining in the lumen of the tube is as semicircular in shape as is the cross-section of the body inserted in the lumen, but displaced by 180 degrees from said body. If the axis of symmetry of the lumen of the tube is simultaneously the rotation axis of the coupling device, the center of the straight portion of the border of the cross-section of the hollow space lies on the rotation axis of the coupling device.

In somewhat general terms, the border of the cross-section of the cylindrical hollow space includes a portion that is point-symmetrical with the point of intersection of the rotation axis with the border of the cross-section. For example, the cylindrical hollow space has a semi-elliptical, right-angle, or three-cornered cross-section, so that the point-symmetrical portion is also straight in these cases. The point-symmetrical portion of the border of the cross-section can also be S-shaped, for example.

In addition, the cross-section of the cylindrical hollow space can have any shape. For form-locked transmission of torque, the cross-section is not circular-shaped. Transmission of torque is also possible with a circular cross-section if the center point of the circular cross-section does not lie on the rotation axis of the coupling device.

The described embodiments of the coupling device, depending on the material of the coupling device, its method of production, the torque to be transmitted, and other parameters, have a series of advantages. In particular, in many cases they can be produced particularly simply and thus economically. The aforementioned point-symmetry and in particular the semicircular-shaped cross-section produce in especially simple manner an economically producible coupling device with little play.

The drive unit can be configured so that it can be connected with the medical resector—in particular with a shaft or a drain chamber of the medical resector—in such a way that a rotation axis of the coupling device is not parallel to a longitudinal axis of the medical resector, in particular of the shaft of the medical resector. This non-parallelism includes in particular a departure from the parallelism that exceeds the precision that is customary in medical technology or the tolerances that are customary in medical technology. In particular, between the longitudinal axis of the medical resector or of its shaft on the one hand and the rotation axis of the coupling device of the drive unit on the other hand, there is an angle of at least 0.4 degree, in particular an angle between 0.6 and 1.0 degree.

As already mentioned, the coupling device is configured on the drive unit to transmit the rotation movement generated by the engine device to an axle coupled with the rotatable high-frequency electrode on a resector. For this purpose on the proximal end of the axle a coupling device is provided that corresponds to the coupling device of the drive unit. Said coupling device is designated hereafter as a coupling device on the resector side.

The aforementioned angle between the rotation axis of the coupling device of the drive unit on the one hand and the longitudinal axis of a resector that is to be coupled with the drive unit on the other hand is adapted in particular to an angle between the rotation axis of the rotatable high-frequency electrode or of the axle between high-frequency electrode and the resector-side coupling device on the one hand and the longitudinal axis of the medical resector or of its shaft on the other hand. The angles are in particular adapted in such a way that the rotation axis of the coupling device of the drive unit and the rotation axis of the resector-side coupling device coincide.

Such an angle or such a non-parallelism on a medical resector makes possible a central positioning of the rotatable high-frequency electrode on the distal end on the one hand and simultaneously an eccentric positioning of the end of the axle and of the coupling device positioned thereon on the resector side on the proximal end of the medical resector on the other hand. The central positioning of the axle and of the resector-side coupling device on the proximal end creates a maximum distance, for example, from a shaft of an endoscope that can be inserted in the shaft of the medical resector and thus maximum building space for the drive unit.

A coaxial alignment of the rotation axis of the rotatable high-frequency electrode, the axle, and the resector-side coupling device on the one hand and the rotation axis of the coupling device of the drive unit on the other hand allows a construction that is especially low in friction and thus also in loss and abrasion. With the corresponding configuration of the coupling devices of the drive unit and the medical resector, a small difference in the angle up to a few degrees can be compensated by the coupling devices. In this case, despite a non-parallel arrangement of the rotation axis of the axle of the medical resector to the longitudinal axis of the medical resector, the drive unit can be configured for an arrangement in which the rotation axis of the coupling device of the drive unit is parallel to the longitudinal axis of the medical resector.

A drive device as described above can also comprise a locking device for locking the coupling device of the medical resector in the drive unit. The locking device is configured, in particular, so as not to rotate with the coupling device. The locking device in particular includes a spring-loaded bolt, which is configured to engage in a groove on the axle. This bolting device can be positioned so that it borders immediately on the distal side on the coupling device. Not only does this make possible an especially compact structure, but it also reduces the play and the influence of elasticities on the mechanical interplay of the coupling device of the drive unit on the one hand and a resector-side coupling device on the other hand. As a result, both the locking device and the coupling device can operate with special precision and without play.

The spring-loaded bolt is configured in particular in the form of a slide bar. Said slide bar can have a circular-shaped cross-section at both ends and thus can be guided precisely into a corresponding borehole. In a central area it is, for example, square-shaped with a hole, aperture, or recess. Said hole, aperture, or recess is configured in such a way that at least in one position of the bolt a coupling device of a medical resector can be guided through it. If the resector-side coupling device engages in the coupling device of the drive unit in the manner foreseen, a border of the hole, aperture, or recess of the bolt can engage in a surrounding groove on the resector-side coupling device. As a result, the bolt locks the resector-side coupling device in the coupling device of the drive unit. Owing to the spring-loading, the bolt is held in this locking position for as long as it is not pushed manually against the spring-loading into a position in which the resector-side coupling device can again be pulled out.

The described locking device with a spring-loaded bolt, depending on the requirements to be met, can be produced in a manner that is especially simple and economical as well as robust and precise.

A coupling device of a drive unit as described above can, in addition, be configured in order to transmit an electric signal, in particular an electric high-frequency signal, and thus electrical high-frequency current, from the drive unit to the axle of a medical resector coupled with the drive unit. The described drive unit can thus fulfill several functions simultaneously, in particular simultaneously transmitting a rotation movement and an electric signal to the axle of the medical resector and via the axle to the rotatable high-frequency electrode. This assumes a corresponding configured resector-side coupling device. In particular, both coupling devices comprise a metal or another electricity-conducting material. Thus there is no longer any necessity to feed the electric signal on the medical resector and to provide a device on the medical resector for transmitting an electric signal to the axle.

To transmit the electric signal to the coupling device, a contacting device in particular is provided on or in the drive unit. Said contacting device includes one or more sliding contacts, which are contiguous with a mantle flange of the coupling device. Positioning the sliding contact on the mantle surface of the coupling device can require an especially compact structure for the entire drive unit. Thus a coupling device, a locking device, and a contacting device can be realized in the smallest area. Instead of a contacting device with sliding contact, a transmission of the electric signal is possible via the described locking device directly to the resector-side coupling device.

The drive unit can be configured to be connected in immediate, fluid-insulated, and detachable manner with a drain chamber on the proximal end of the shaft of a medical resector. For this purpose the drive unit has, in particular, a geometric shape that corresponds to that of the drain chamber, and an insulating device. The immediate, fluid-insulated, and detachable connection of the drive unit with the drain chamber makes possible a structure of the medical resector that is especially simple and economical to produce and an especially small structural length.

A medical resector for cutting, ablating, or coagulating human or animal tissue includes a rotatable high-frequency electrode on the distal end of a shaft of the medical resector, a coupling device on the proximal end of the shaft, and an axle that connects the coupling device with the rotatable high-frequency electrode. The coupling device is configured for detachable mechanical coupling with a drive unit, in particular a drive unit that produces a rotation frequency in a range from 10 rpm to 200 rpm. The coupling device is in particular configured for detachable mechanical coupling with one of the drive units described above.

The described medical resector makes possible, in particular together with the aforementioned drive unit, a particularly simple and economic construction and an especially small structural length. Advantages of the drive unit heretofore described apply also to a combination of the drive unit and the medical resector, and partially as well to the medical resector alone.

The coupling device of the medical resector can include a cylindrical portion that is not symmetrical with the rotation axis of the coupling device. A cylindrical portion is a portion that is cylindrical or essentially cylindrical. The cylindrical portion then is not symmetrical with the rotation axis of the coupling device if departures from symmetry are caused not just by cams or the like, as these are sometimes employed with conventional coupling devices as a tappet or for catch locking.

The cylindrical portion can engage in a correspondingly configured portion of a hollow cavity on a corresponding coupling device of the medical resector. The cylindrical portion of the coupling device of the medical resector has, for example, a cross-section whose border includes a portion that is straight or is point-symmetrical with the point of intersection of the rotation axis with the border of the cross-section. For example, the cylindrical portion has a semi-circular, semi-elliptical, right-angle, or three-cornered cross-section.

The rotation axis of the coupling device of the medical resector can lie on a portion of the border of the cross-section of the hollow cavity of the coupling device that is straight or is point-symmetrical with the point of intersection of the rotation axis with the border of the cross-section.

The axle of the medical resector can have a rotation axis that is not parallel with a longitudinal axis of the medical resector or of a shaft of the medical resector.

A medical resector as described above can include one of the aforementioned drive units. In addition the medical resector can be combined with an endoscope to form a resectoscope, so that a shaft of the endoscope is positioned in a channel in the shaft of the medical resector.

BRIEF DESCRIPTION OF THE DRAWINGS

Hereafter, embodiments are described more closely with reference to the appended drawings, which are as follows.

DETAILED DESCRIPTION OF THE INVENTION

Figure 1:
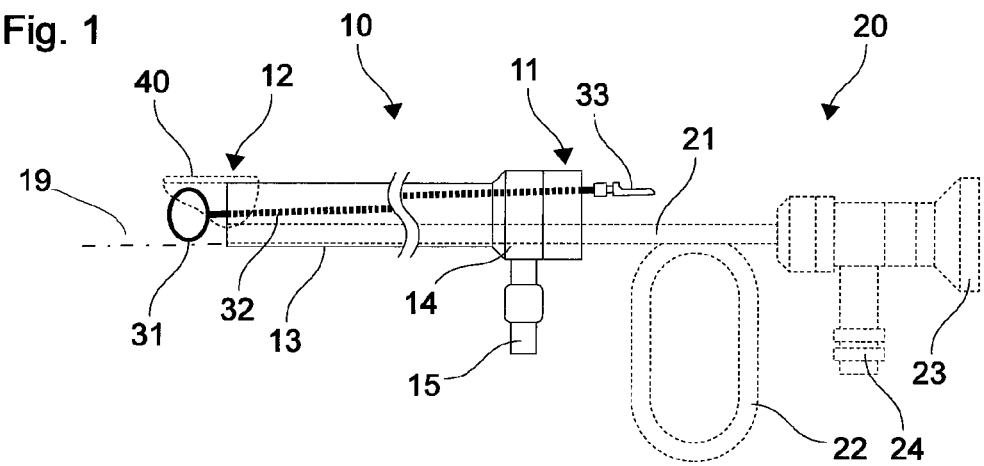
FIG. 1 shows a schematic sketch of a medical resector with an endoscope.

FIG. 1 shows a schematic sketch of a medical resector 10 for cutting, ablating, or coagulating human or animal tissue, having a proximal end 11, a distal end 12, and a shaft 13 that extends from the proximal end 11 to the distal end 12. The shaft 13 is cylindrical with a circular, elliptical, oval, or any other-shaped cross-section. The longitudinal axis of the shaft 13 is parallel to the plane of projection of FIG. 1.

On its proximal end 11 the medical resector comprises a drain chamber 14 having a connection 15 for a suction device that is not shown in FIG. 1. An endoscope 20 or its shaft 21 can be inserted into the drain chamber 14 and the shaft 13. In addition the medical resector 10 can comprise a corresponding channel with openings on both ends, which extends through the drain chamber 14 and the shaft 13 from the proximal end 11 to the distal end 12 of the medical resector.

The medical resector 10 can also be used without the endoscope 20. The endoscope 20 is therefore shown with broken lines. However, the medical resector 10 and the endoscope 20 together form a frequently used combination, which is also referred to as a resectoscope. The surface that is to be ablated or coagulated can be observed through the endoscope before use and also during the use of the medical resector and the effect of the resector 10 is immediately observed.

The endoscope 20 includes the aforementioned shaft 21, a grip 22 that improves the manual operation of the endoscope 20 or another handle, an eyepiece 23, and a coupling 24 for connecting the endoscope 20 with a light source that is not shown in FIG. 1. Alternatively the grip 22 or another handle differing from that shown in FIG. 1 is positioned on a shaft, into which the shaft 21 of the endoscope can be inserted and, in particular, can be fastened or locked there. The endoscope 20 can be guided independently of the medical resector 10, for instance by being rotated in the medical resector 10, with the grip 22 or another handle on the endoscope 20 or alternatively on a shaft in which the shaft 21 of the endoscope 20 is guided and held.

The medical resector 10 also includes a rotatable high-frequency electrode 31 on its distal end 12. The rotatable high-frequency electrode 31 is fastened on an axle 32 or produced as a single unit with said axle 32. The axle 32 extends, on the interior of the shaft 13 of the medical resector 10 from the rotatable high-frequency electrode 31 on the distal end 12 to a coupling 33 on the proximal end 11. The coupling 33 is positioned proximally to the drain chamber 14. The axle 32 is configured to transmit a rotation of the coupling 33 to the high-frequency electrode 31. One or more bearings and/or a guide tube, extending from the proximal end 11 to the distal end 12 of the medical resector 10, are provided for rotatable mounting of the axle 32. The bearings and guide tube are not shown in FIG. 1.

The axle 32 and thus also the rotation axis of the rotatable high-frequency electrode 31, of the axle 32, and of the coupling device 33 are not parallel to the longitudinal axis of the shaft 13. The rotation axis and the longitudinal axis 19 form an angle of at least 0.4 degree, in particular an angle between 0.6 and 1.0 degree or an angle of essentially 0.8 degree. This angle makes possible, on the one hand, a central positioning of the high-frequency electrode 31 on the distal end 12 and, on the other hand, a maximum distance between the coupling device 33 on the proximal end 11 and the shaft 21 of the endoscope 20.

A funnel collar 40 made of synthetic material, ceramic, or another electrically insulating material is positioned on the distal end 12. The optional funnel collar 40 protects the high-frequency electrode 31 from damage and protects the human or animal tissue from injury by the high-frequency electrode 31, in particular while inserting the medical resector 10. In addition the funnel collar 40 can guide a fluid that exits on the distal end 12 of the medical resector. In addition or alternatively, the funnel collar 40 can channel or concentrate onto the area around the high-frequency electrode 31 a suction effect generated on the distal end 12 of the medical resector 10. In both cases the funnel collar 40 improves the view through the endoscope 20 onto a surface processed by the high-frequency electrode 31.

With the medical application of the resectoscope made up of the medical resector 10 and an endoscope 20 inserted into the latter, rotation frequencies in the previously described range between 30 rpm and 60 rpm have especially proven effective. Depending on the application, the diameter and shape of the rotatable electrode, rotation frequencies have proven effective ranging from 20 rpm, at times even from 10 rpm, to 100 rpm or 150 rpm, at times even up to 200 rpm.

For the rotation frequencies mentioned, on the basis of the considerations and computations outlined above, good results were expected with respect to the cutting capacity and cutting quality. These and other, sometimes surprising advantages were confirmed in extensive, intensive, and therefore also very time-consuming experiments. In particular, at the rotation frequencies cited, an optimum exists concerning ablation capacity on the one hand and observability and controllability of the ablation on the other hand. The oblated tissue fragments are so small that they barely block the view through the endoscope 20 onto the work area, especially since they can be suctioned off and thus removed from the field of vision quickly and without risk of a blockage of the medical resector 10.

In addition, the movement of the high-frequency electrode can be perceived by medical personnel without problem and halted. Observation of a high-frequency electrode rotating in the aforementioned range, in particular between 30 rpm and 60 rpm, is not yet perceived as stressful. Every individual ablated tissue piece and the resulting exposed deeper tissue layers and their surfaces can be pursued or observed. At clearly higher rotation frequencies above 100 rpm and higher, at more than 200 rpm, the movement of the high-frequency electrode and of the tissue pieces and their observation prove increasingly tiring. This is hazardous for medical applications not only involving the medical personnel but also, above all, for the patient.

With the medical resector 10 illustrated in FIG. 1, a drive unit can be coupled with the rotatable high-frequency electrode 31, as described more closely hereafter with reference to FIGS. 2 through 6. Each of FIGS. 2 through 5 shows a schematic view of a section through the drive unit 50. The plane of intersection shown in FIGS. 2 through 5 lies perpendicular to the plane of projection of FIG. 1. To the left here in each case, the distal end or the distal side of the drive unit 50 is shown, while seen to the right is the proximal end or the proximal side. To improve clarity of the images, all reference numbers are not shown in each of FIGS. 2 through 5.

Figure 2:
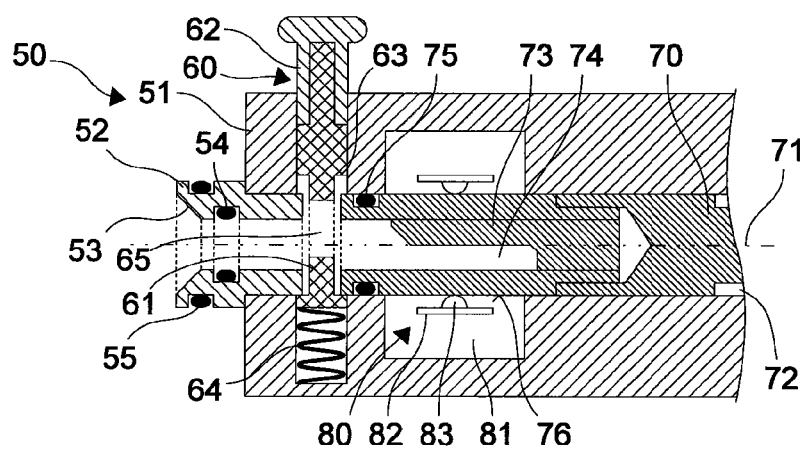
FIG. 2 shows a schematic sketch of a part of a drive unit.

FIG. 2 shows a schematic view of a section of part of the drive unit 50. The drive unit 50 includes a housing body 51, made for instance of synthetic or another electrically insulating material. The housing body 51 comprises several boreholes and hollow spaces, some of which can be seen in FIGS. 2 through 5 and are described hereinafter.

In particular, the housing body 51 comprises an essentially circular-cylindrical longitudinal borehole, which runs from left to right in the view in FIG. 2, or therefore in the direction from distal toward proximal. A conical device 52 is inserted in the distal end of the longitudinal borehole. The conical device 52 comprises a conical surface 53, a clearance hole visible in FIG. 2, and O-rings or other insulating devices 54, 55 inserted in surrounding grooves on the inside or outside.

In addition, the housing body 51 comprises a transverse borehole, which is perpendicular to the longitudinal borehole and runs from above to below in the view in FIG. 2. In this second borehole there is mounted a locking device 60 whose function is more closely described below with reference to FIGS. 3 and 4. The locking device 60 includes a bolt 61 with an insulating cap 62 made of an electrically insulating material on one end that extends beyond the housing body 51. The bolt 61 has an external shape that is adapted at least in sections to the cross-section of the transverse borehole 63 in the housing body 51. Positioned on one end of the bolt 61 that is turned away from the insulating cap 62 is a spring 64 or another elastic element that presses the bolt 61 in the direction of the insulating cap 62. In a center portion the bolt 61 has, at least approximately, the shape of a square with an aperture 65. In the position of the bolt 61 shown in FIG. 2, it is contiguous with the conical installation 52, which protrudes somewhat into the transverse borehole. The spring 64 is thereby prevented from any further expansion.

An axle 70 with a symmetry and rotation axis 71 is positioned in the longitudinal borehole 72 in the housing body 51. The symmetry and rotation axis 71 of the axle 70 is simultaneously the symmetry axis of the conical device 52. When the drive unit 50 is positioned on the medical resector 10 described above with reference to FIG. 1, the rotation axis 71 of the axle 70 corresponds to the rotation axis of the rotatable high-frequency electrode 31, of the axis 32, and of the coupling 33 or describes a small angle with respect to it.

While the conical device 52 is positioned distally from the bolt 61 of the locking device 60, the axle 70 is positioned proximally from the bolt 61. In FIG. 2 the conical device 52 and the axle 70 are each slightly distanced from the bolt 61, in the direction parallel to the rotation axis 71. Alternatively, the conical device 52 and/or the axle 70 can be immediately contiguous with the bolt 61.

On the distal end the axle 70 is configured as a coupling device 73 with a hollow space 74. Accordingly, the axle 70 in the area of the coupling device 73 is constructed of several parts. However, the structure and shape of the axle 70 and in particular of the coupling device 73 can differ from the illustration in FIG. 2. The hollow space is cylindrical at least in parts, as is described in more detail hereinafter, for example, with reference to FIG. 6.

An O-ring in a surrounding groove or another insulating device 75 is provided on the distal end of the axle 70 and of the coupling device 73.

A contacting device 80 is positioned in a hollow space 81. The hollow space 81 surrounds the coupling device 73 or at least borders on it. The contacting device 80 includes one or more contact springs 82 each having one or more sliding contacts 83. The sliding contact or contacts 83 are pressed by the contact springs 82 onto an external mantle surface 76 of the coupling device 73. The contact springs 82 and the sliding contacts 83 are configured so as to constitute an electrically conductive connection between the resting contact springs 82 and the rotating coupling device 73. To prevent oxidation of the surfaces and to make possible a good contacting, the mantle surface 76 of the coupling device and the sliding contacts 83 are, for instance, gilded.

Figure 3:
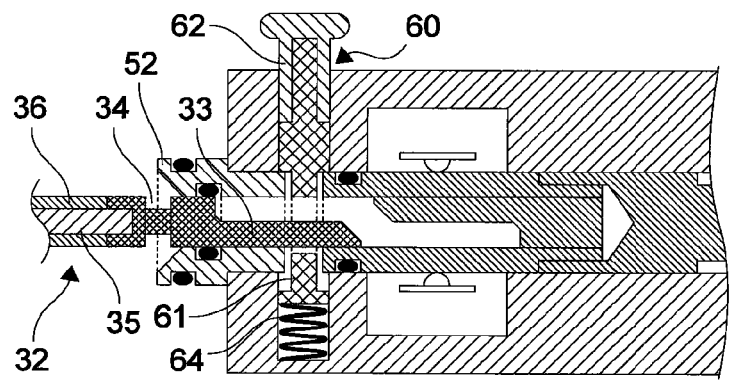
FIG. 3 shows a schematic sketch of a part of the drive unit from FIG. 2.

FIG. 3 shows a schematic view of the drive unit 50, corresponding to a great extent to the view in FIG. 2. In a departure from FIG. 2, however, a coupling device 33 in the situation shown in FIG. 3, as already described above with reference to FIG. 1, is partly inserted in the conical device 52, the aperture 65 in the bolt 61, and the coupling device 73 of the drive unit 50. For this purpose the bolt 61 is pushed so far by pressure on the insulation cap 62 that the coupling 33 can move through the aperture 65 in the bolt 61.

The coupling 33 comprises a surrounding groove 45. On the distal end of the coupling 33, said groove continues into the axle 32 illustrated in FIG. 2 or is fastened to it. The axle 32 includes an electrically conductive core, for instance a rod 35 of metal that can be welded or soldered together with the coupling 33. In addition the axle includes an insulating mantle 36 that surrounds the rod 35 and provides electrical insulation.

Figure 4:
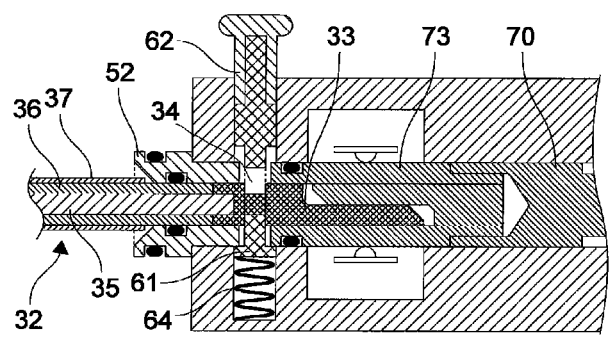
FIG. 4 shows a schematic sketch of a part of the drive unit from FIG. 2.

FIG. 4 shows another schematic depiction, which corresponds to great extent to FIGS. 3 and 4. Unlike FIG. 3, however, in FIG. a situation is presented in which the coupling device 33 of the medical resector is inserted so far into the coupling device 73 of the drive unit 50 that the bolt 61 is pressed by the spring 64 into the groove 34 on the coupling device 33 of the medical resector and engages in it. The bolt 61 of the locking device 60 locks the coupling device 33 of the medical resector in the coupling device 73 of the drive unit 50 in the position shown in FIG. 4. This locking can be released if the bolt 61 is pushed by pressure on the insulation cap 62 against the force of the spring 64 into the position shown above in FIG. 3.

It can further be recognized in FIG. 4 that the axle 32 comprises a tube 37 of metal or another rigid material, which surrounds the insulating mantle 36. The tube 37 increases the robustness and torsion-rigidity of the axle 32 and reduces its elasticity.

Figure 5:
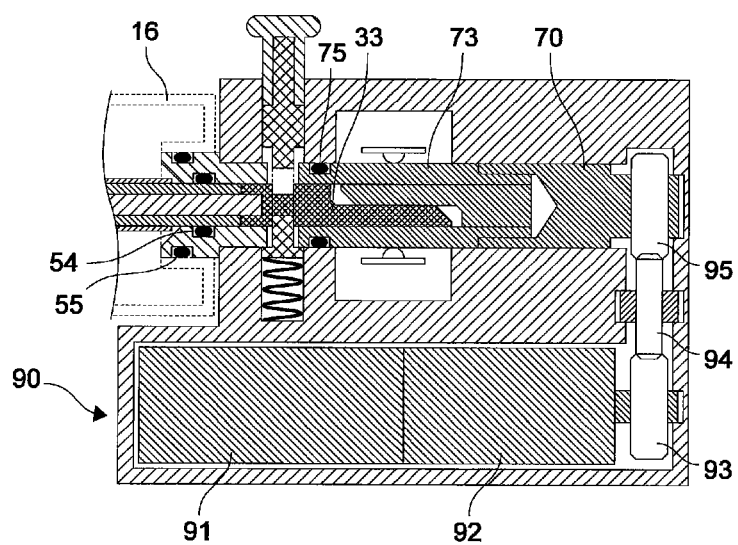
FIG. 5 shows a schematic sketch of the drive unit from FIG. 2.

FIG. 5 shows a schematic view of a section through the entire drive unit 50. The illustrated position of the coupling 33 of the medical resector in the coupling device 73 of the drive unit 50 and the locking of the coupling device 33 of the medical resector in this position correspond to the preceding description with reference to FIG. 4.

Contrary to FIGS. 2 through 4, FIG. 5 also shows an engine device 90, which is likewise integrated into the housing body 51 of the drive unit 50. Said engine device 90 includes an electric engine 91 and a reduction gear 92. The reduction gear 92 is coupled by toothed wheels 93, 94, 95 with the axle 70. Consequently the electric engine 91, by the reduction gear 92 and the toothed wheels 93, 94, 95, can drive the axle 70 and in particular the coupling device 73 of the drive unit 50 as well as the coupling device 33 and the axle 32 of the medical resector that is coupled with the drive unit 50.

FIG. 5 also shows a wall of the drain chamber 14 previously introduced with reference to FIG. 1. It can be recognized that the wall 16 is contiguous with the conical device 52. The gap between the wall 16 and the conical device 52 is insulated against fluids by the insulating device 55. Solid, liquid, or gaseous material suctioned by the shaft 13 and the drain chamber 14 therefore cannot exit at this spot. The insulating device 54 correspondingly prevents fluid from overflowing between the axle 32 and the conical device 52 in the direction toward the locking device 60. The hollow space 81 in the housing body 51 in which the contact spring 82 and the sliding contacts 83 are positioned is once again protected in addition by the insulation device 75 from penetration by fluids.

The entire arrangement is especially compact owing to the integration of the locking device 60, coupling device 73, and sliding contacts 83 in very narrow space. Another contributing factor is that the engine 91 and gear 92 are positioned beside rather than proximal to the coupling device 73.

Figure 6:
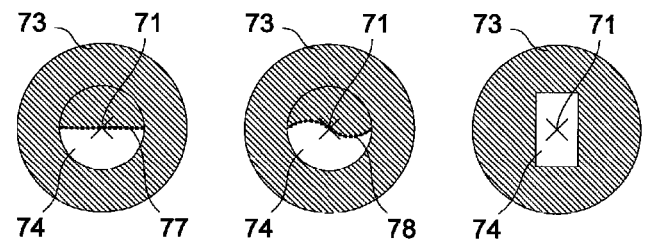
FIG. 6 shows a schematic sketch of cross-sections of coupling devices.

FIG. 6 shows schematic renderings of cross-sections of three embodiments of the coupling device 73. Displayed in each case is a section along a plane that is perpendicular to the rotation axis 71, described above with reference to FIG. 2, of the axle 70 and of the coupling device 73. The cutting plane is, for instance, in the area of the sliding contacts 83.

In the example illustrated in FIG. 6 left, the hollow space 74 has a semicircular-shaped cross-section. The border of the semicircular cross-section comprises a straight portion 77 that is shown in dotted outline and that is cut in the center by the rotation axis 71 of the axle 70 and of the coupling device 73. The straight portion 77 of the border of the cross-section of the hollow space 74 is thus point-symmetrical with its point of intersection with the rotation axis 71 of the coupling device 73.

In the example illustrated in the center of FIG. 6, the hollow space 74 has a cross-section with an S-shaped portion 78 that is shown in dotted outline and is point-symmetrical with the point of intersection of the rotation axis 71 and of the border of the cross-section 74, in particular point-symmetrical with the point of intersection of the rotation axis 71 and of the S-shaped portion 78 of the border of the cross-section.

In the example illustrated in FIG. 6 at right, the hollow space 74 has a rectilinear cross-section that is symmetrical with the rotation axis 71. Other coupling shapes are possible besides those illustrated in FIG. 6.

What is claimed is:

1. A drive unit for a rotatable high-frequency electrode of a medical resector for cutting, ablating, or coagulating human or animal tissue, having:
    an engine device for generating a rotation movement;
    a coupling device for transmitting the rotation movement generated by the engine device to an axle coupled with a rotatable high-frequency electrode when the drive unit is coupled with a medical resector; and
    a locking device for locking the coupling device of the medical resector in the drive unit, wherein the locking device includes a spring-loaded bolt that is configured to engage in a groove in an axle of the medical resector,
    wherein the drive unit is configured to provide on the coupling device a rotation frequency in a range from 10 revolutions per minute to 200 rpm.

2. The drive unit according to claim 1, wherein the engine device comprises a reduction gear.

3. The drive unit according to claim 1, wherein the coupling device includes a hollow space with a cylindrical portion that is not symmetrical with the rotation axis of the coupling device.

4. The drive unit according to claim 1, wherein the drive unit is configured to provide on the coupling device a rotation frequency in a range from 30 rpm to 60 rpm.

5. The drive unit according to claim 1, wherein the drive unit is configured to be mechanically connected with the medical resector in such a way that a rotation axis of the coupling device is not parallel with a longitudinal axis of the medical resector.

6. The drive unit according to claim 1, wherein the locking device is configured not to rotate with the coupling device.

7. The drive unit according to claim 1, wherein the spring-loaded bolt comprises an aperture or a recess in which an axle of the medical resector is positioned when the medical resector is coupled with the drive unit.

8. The drive unit according to claim 1, wherein the coupling device is also configured to transmit an electric high-frequency signal from the drive unit to an axle of the medical resector.

9. The drive unit according to claim 1, in addition with:
a contacting device for transmitting an electric high-frequency signal to the coupling device, wherein the contacting device includes a sliding contact that is contiguous with a mantle surface of the coupling device.

10. The drive unit according to claim 1, wherein the drive unit is configured to be connected directly, in fluid-insulated and detachable manner with a drain chamber.

* * * * *